United States Patent
Noordvyk et al.

(10) Patent No.: US 10,078,726 B2
(45) Date of Patent: Sep. 18, 2018

(54) IMAGE PROCESSING SYSTEM AND METHOD FOR DETECTING AN ANATOMICAL MARKER WITHIN AN IMAGE STUDY

(71) Applicant: Change Healthcare Holdings, LLC, Nashville, TN (US)

(72) Inventors: Allan Noordvyk, Surrey (CA); Mahmoud Ramze Rezaee, North Vancouver (CA); Jay Waldron Patti, Charlotte, NC (US)

(73) Assignee: Change Healthcare Holdings, LLC, Nashville, TN (US)

( * ) Notice: Subject to any disclaimer, the term of this patent is extended or adjusted under 35 U.S.C. 154(b) by 51 days.

(21) Appl. No.: 15/086,725

(22) Filed: Mar. 31, 2016

(65) Prior Publication Data

US 2017/0286598 A1 Oct. 5, 2017

(51) Int. Cl.
*G06K 9/00* (2006.01)
*G06F 19/00* (2018.01)
*G06T 7/00* (2017.01)
*G16H 50/50* (2018.01)

(52) U.S. Cl.
CPC .......... *G06F 19/321* (2013.01); *G06T 7/0012* (2013.01); *G16H 50/50* (2018.01); *G06T 2207/10088* (2013.01); *G06T 2207/30204* (2013.01)

(58) Field of Classification Search
CPC . G06F 19/321; G06F 19/3437; G06T 7/0012; G06T 2207/10088; G06T 2207/30204
See application file for complete search history.

(56) References Cited

U.S. PATENT DOCUMENTS

| | | | | |
|---|---|---|---|---|
| 7,564,999 B2 * | 7/2009 | Luo | ............... | G06K 9/38 382/128 |
| 8,036,435 B2 * | 10/2011 | Partain | ............... | G06T 7/0012 382/128 |
| 8,121,368 B2 * | 2/2012 | Wiersma | ............... | G06T 7/251 382/128 |
| 9,292,761 B2 * | 3/2016 | Hamada | ............... | G06K 9/46 |

* cited by examiner

*Primary Examiner* — Shefali Goradia
(74) *Attorney, Agent, or Firm* — Alston & Bird LLP

(57) ABSTRACT

A method, image processing system and computer program product are provided for detecting an anatomical marker within an image study. In the context of a method, data elements associated with image slices of the image study of a patient are accessed. The data elements are representative of one or more characteristics of the image slices, but do not include picture elements that comprise the image slices. The method also includes reviewing the data elements associated with at least some image slices of the image study of the patient. The method further includes detecting the anatomical marker within the image study based upon a review of the data elements and identifying a subset of the image slices of the image study based upon the anatomical marker or a distance from the anatomical marker.

19 Claims, 5 Drawing Sheets

IMAGE PROCESSING SYSTEM AND METHOD FOR DETECTING AN ANATOMICAL MARKER WITHIN AN IMAGE STUDY

TECHNOLOGICAL FIELD

An example embodiment relates generally to the review of an image study comprised of a plurality of image slices and, in particular, to the detection of an anatomical marker within an image study in order to permit a subset of the image slices of the image study to be identified based upon the anatomical marker.

BACKGROUND

Image studies of a patient may be captured by a plurality of different cross-sectional imaging modalities, such as computed tomography (CT) imaging, magnetic resonance (MR) imaging and the like. The image study may include a plurality of image slices captured at different locations along a patient's body. For example, a patient lying on a table may undergo an image scan with image slices captured at each of a plurality of discrete locations. As a more particular example, the image study of the abdomen of a patient may include a plurality of image slices including image slices of the upper abdomen, images slices of the mid-abdomen and image slices of the lower abdomen. As another example, the image study of the head of a patient may begin with image slices at the top of the patient's head and conclude with image slices of the patient's neck.

While each image slice is two dimensional, an image study formed of a plurality of image slices provides a three-dimensional volumetric view of the patient and may be analyzed by a physician or other health care professional in order to assess the condition of the patient, such as for purposes of diagnosis or the determination of the effectiveness of a treatment. While image studies comprised of a plurality of image slices are advantageous in regards to the wealth of information that such image studies provide, this same wealth of information may introduce difficulties or inefficiencies for a physician or other health care professional who is reviewing an image study. In this regard, a physician or other health care professional may have to review a substantial number of the image slices of an image study in order to find the subset of image slices that are most relevant to the evaluation of the patient. This review may be time consuming and taxing as the physician or other health care professional must attentively review numerous image slices to identify those of most interest.

In order to facilitate the identification of the subset of image slices that is of most interest, techniques for fiducial or anatomic landmark detection have been developed. These techniques review the image slices captured by cross-sectional imaging modalities, such as CT and MR imaging modalities, in order to identify particular features, termed fiduciary markers or anatomical landmarks, within the image study. Once the particular features have been identified within the image study, a physician or other health care professional may more efficiently review the image study by focusing their review upon a subset of image slices that are located in a known relationship to the identified features. For example, an image study of the torso of a patient may be subjected to fiducial or anatomic landmark detection techniques which serve to identify the location of the chest and the abdomen within the image study. Thus, a physician reviewing the image study may more quickly locate the image slices that represent the stomach, based upon the relative location of the stomach (which resides within the abdomen) with respect to the lungs (which reside in the chest), so as to facilitate their review of the relevant portion of the image study.

Fiducial or anatomic landmark detection techniques utilize three-dimensional volumetric image processing and/or analysis techniques in order to analyze the image slices of an image study. As such, fiducial or anatomic landmark detection techniques are relatively complex and employ substantial computing resources in order to detect the desired fiducial or anatomic markers. In this regard, the complexity of the fiducial or anatomic landmark detection techniques may increase depending upon the nature of the fiducial or anatomic markers with many image slices being required to be subjected to the image processing and analysis techniques. Fiducial or anatomic landmark detection techniques rely upon image analysis of the picture elements (pixels) of one or more image slices of an image study. Thus, these techniques not only require access to the values of the picture elements of the different image slices, but also generally require the processing of substantial amounts of data, such as the analysis of large numbers of pixel intensity values for model matching or other purposes. Thus, these fiducial or anatomic landmark detection techniques require substantial processing power and utilize relatively large amounts of memory. However, as a result of the three-dimensional volumetric image processing and analysis performed by such fiducial or anatomic landmark detection techniques, the fiducial or anatomic markers may be identified with reasonable precision, thereby effectively guiding the review of an image study by a physician or other health care professional.

BRIEF SUMMARY

A method, image processing system and computer program product are provided in accordance with an example embodiment in order to detect an anatomical marker within an image study. In this regard, the method, image processing system and computer program product of an example embodiment may be configured to detect an anatomical marker based upon data elements that are representative of one or more characteristics of the image slices, but that do not include picture elements. Thus, the method, image processing system and computer program product of this example embodiment may detect an anatomical marker in a more timely and efficient manner. Consequently, the processing resources required to detect an anatomical marker may be conserved, while still permitting a subset of the image slices of the image study to be reliably identified based upon the anatomical marker or a distance from the anatomical marker, such as for storage, display or the like.

In an example embodiment, a method is provided for detecting an anatomical marker within an image study. The method includes accessing data elements associated with image slices of the image study of a patient. The data elements are representative of one or more characteristics of the image slices, but do not include picture elements that comprise the image slices. The method also includes reviewing the data elements associated with at least some image slices of the image study of the patient. The method further includes detecting the anatomical marker within the image study based upon a review of the data elements and identifying a subset of the image slices of the image study based upon the anatomical marker or a distance from the anatomical marker. The method of an example embodiment may also include causing the subset of the image slices to be preferentially presented relative to other image slices of the image study.

In regards to accessing data elements, the method of an example embodiment accesses metadata associated with the image slices of the image study. The metadata includes the data elements. In an example embodiment, the data elements include parameters associated with an imaging system that captures the image slices including parameters that define a configuration of the imaging system during capture of the respective image slices. For example, the data element associated with a respective image slice includes a tube current at which the respective image slice was captured. In an example embodiment, the data elements are reviewed by determining a rate of change of one or more parameters associated with two or more image slices and the anatomical marker is detected based at least in part upon the rate of change. The method of an example embodiment also includes normalizing the data elements associated with the image slices of a plurality of image studies and combining the data elements, following normalization, to create a model of the image studies. In this embodiment, the method reviews the data elements by comparing the data elements to the model.

In another example embodiment, an image processing system is provided that is configured to detect an anatomical marker within an image study. The image processing system includes processing circuitry configured to access data elements associated with image slices of the image study of a patient. The data elements are representative of one or more characteristics of the image slices, but do not include picture elements that comprise the image slices. The processing circuitry is also configured to review the data elements associated with at least some image slices of the image study of the patient. The processing circuitry is further configured to detect the anatomical marker within the image study based upon a review of the data elements and identify a subset of the image slices of the image study based upon the anatomical marker or a distance from the anatomical marker. The processing circuitry of an example embodiment may also be configured to cause the subset of the image slices to be preferentially presented relative to other image slices of the image study.

In regards to accessing data elements, the processing circuitry of an example embodiment is configured to access metadata associated with the image slices of the image study. The metadata includes the data elements. In an example embodiment, the data elements include parameters associated with an imaging system that captures the image slices including parameters that define a configuration of the imaging system during capture of the respective image slices. For example, the data element associated with a respective image slice includes a tube current at which the respective image slice was captured. In an example embodiment, the processing circuitry is configured to review the data elements by determining a rate of change of one or more parameters associated with two or more image slices and the processing circuitry is configured to detect the anatomical marker based at least in part upon the rate of change. The processing circuitry of an example embodiment is also configured to normalize the data elements associated with the image slices of a plurality of image studies and to combine the data elements, following normalization, to create a model of the image studies. In this embodiment, the processing circuitry is also configured to review the data elements by comparing the data elements to the model.

In a further example embodiment, a computer program product is provided for detecting an anatomical marker within an image study. The computer program product includes at least one non-transitory computer-readable storage medium bearing computer program instructions embodied therein for use with a computer. The computer program instructions include program instructions which, when executed, cause the computer at least to access data elements associated with image slices of the image study of a patient. The data elements are representative of one or more characteristics of the image slices, but do not include picture elements that comprise the image slices. The computer program instructions also include program instructions configured to review the data elements associated with at least some image slices of the image study of the patient. The computer program instructions further include program instructions configured to detect the anatomical marker within the image study based upon a review of the data elements and to identify a subset of the image slices of the image study based upon the anatomical marker or a distance from the anatomical marker. The computer program instructions of an example embodiment also include program instructions configured to cause the subset of the image slices to be preferentially presented relative to other image slices of the image study.

In regards to accessing data elements, the program instructions of an example embodiment are configured to access metadata associated with the image slices of the image study. The metadata includes the data elements. In an example embodiment, the data elements include parameters associated with an imaging system that captures the image slices including parameters that define a configuration of the imaging system during capture of the respective image slices. For example, the data element associated with a respective image slice includes a tube current at which the respective image slice was captured. In an example embodiment, the program instructions are configured to review data elements by determining a rate of change of one or more parameters associated with two or more image slices and the program instructions are configured to detect the anatomical marker based at least in part upon the rate of change. The computer program instructions of an example embodiment also include program instructions configured to normalize the data elements associated with the image slices of a plurality of image studies and program instructions configured to combine the data elements, following normalization, to create a model of the image studies. In this embodiment, the program instructions are configured to review the data elements by comparing the data elements to the model.

BRIEF DESCRIPTION OF THE DRAWINGS

Figure 1:
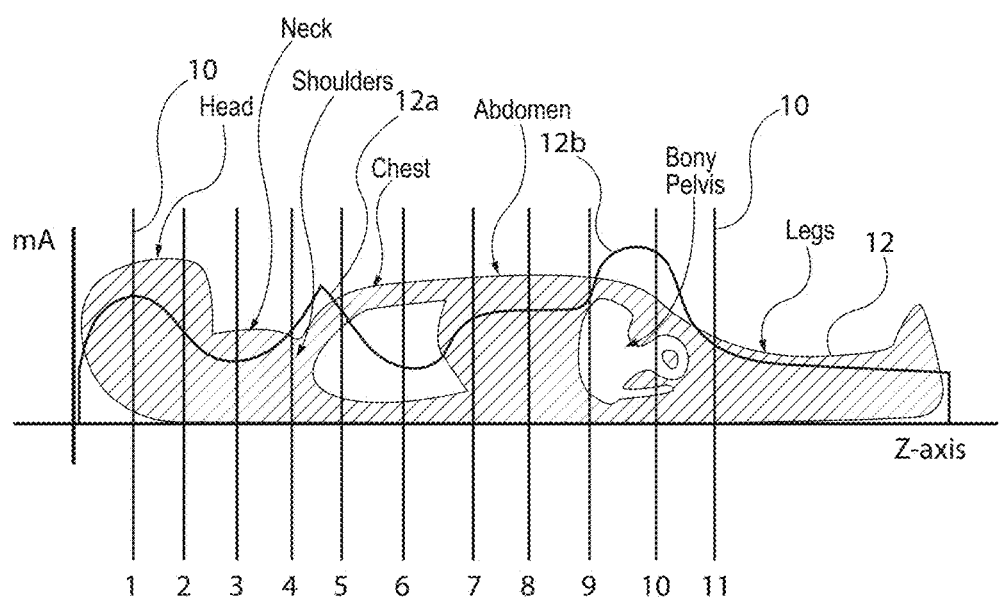
Figure 2:
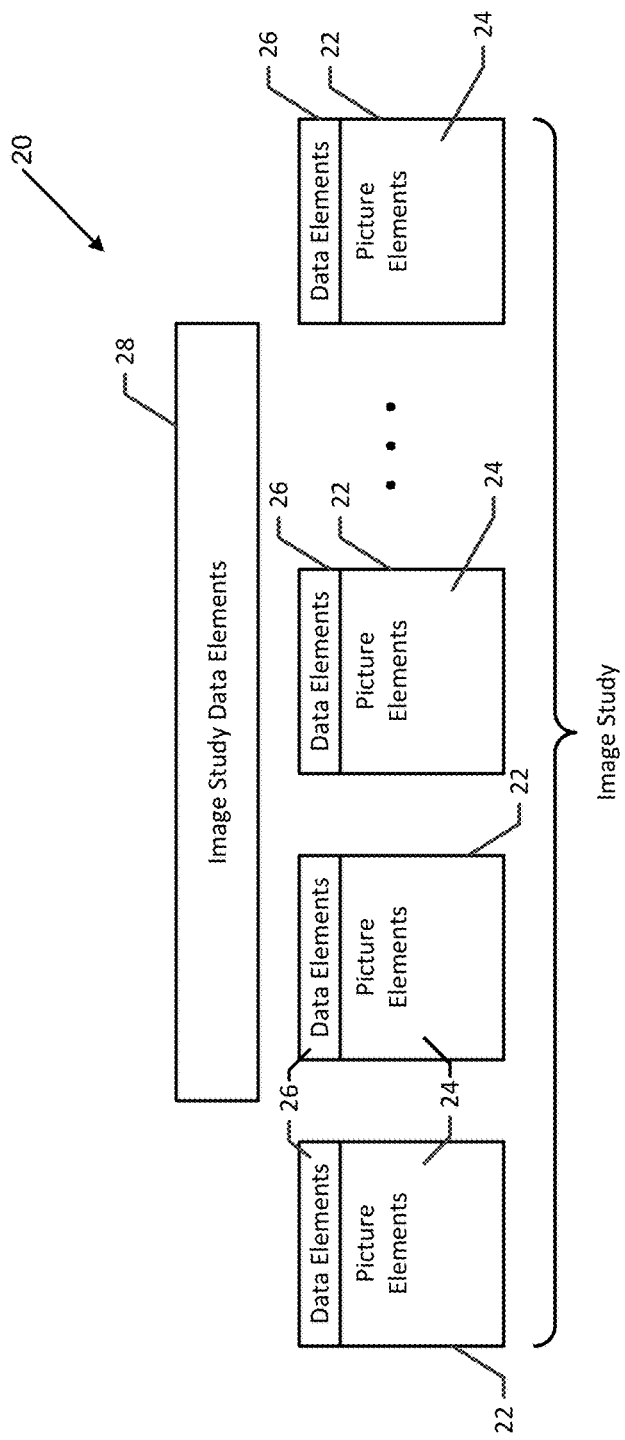
Figure 3:
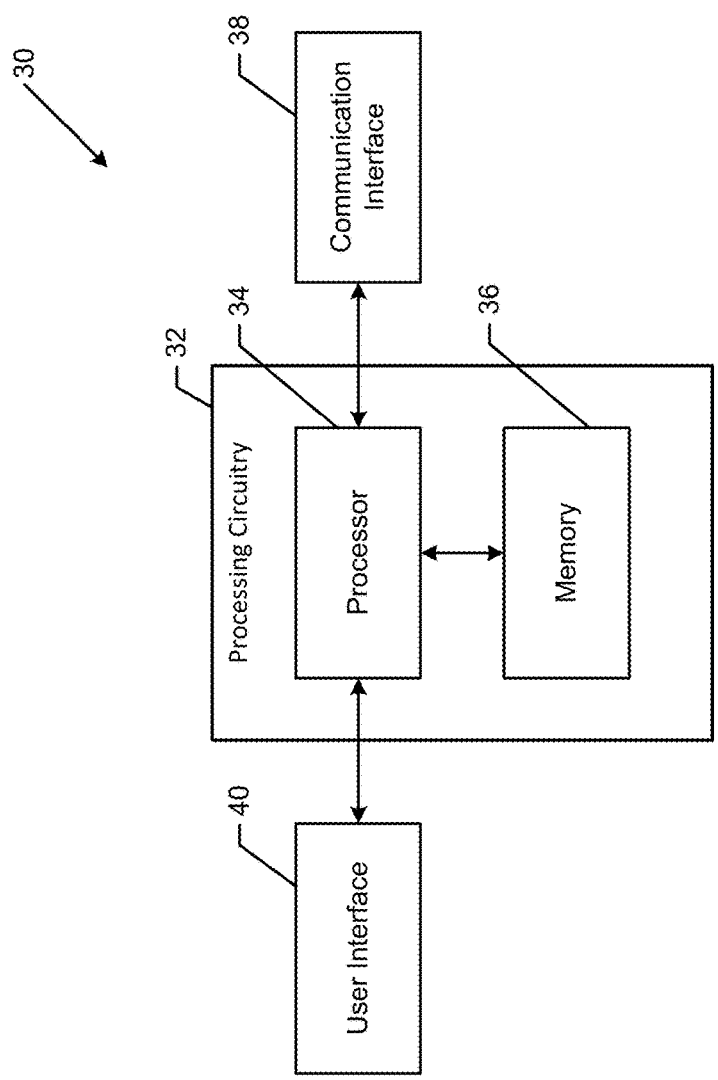
Figure 4:
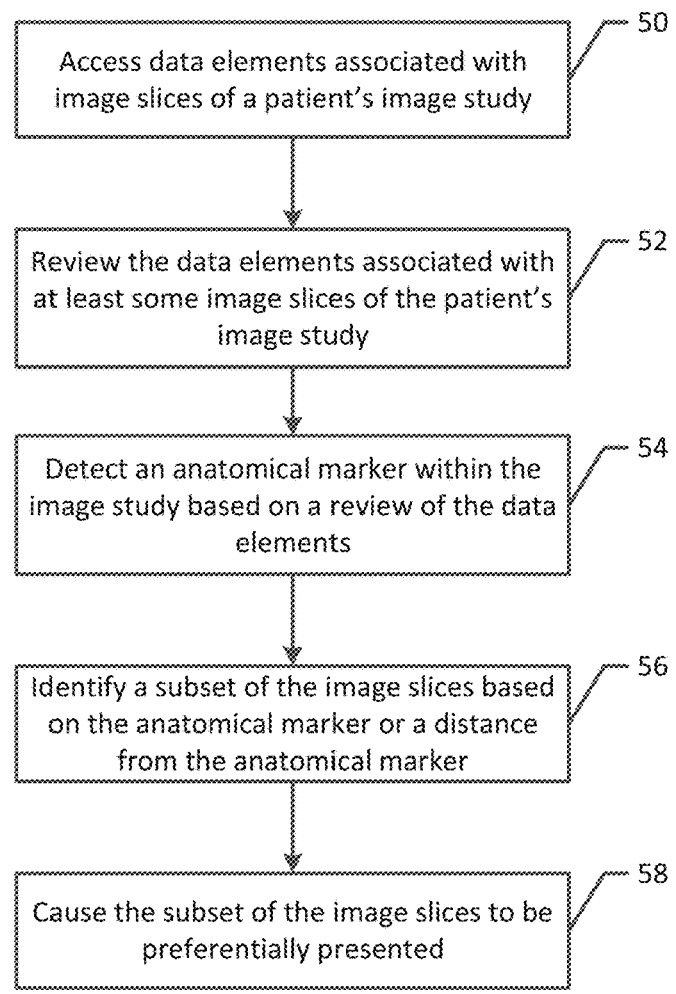
Figure 5:
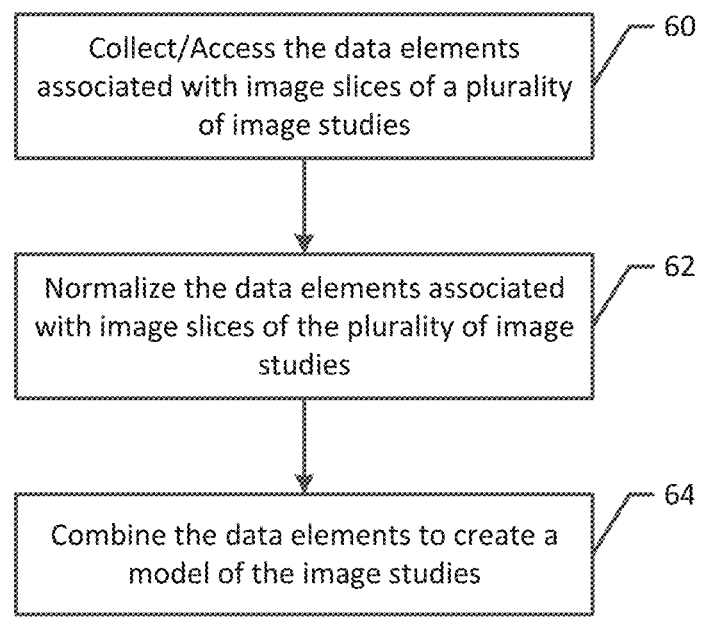

Having thus described certain example embodiments of the present invention in general terms, reference will hereinafter be made to the accompanying drawings which are not necessarily drawn to scale, and wherein:

FIG. 1 graphically depicts variations in a data element, such as the tube current, associated with each of a plurality of image slices of an image study;

FIG. 2 depicts an image study including a plurality of image slices whereby both the image study and each of the constituent image slices include metadata associated therewith;

FIG. 3 is a block diagram of an image processing system that may be specifically configured in accordance with an example embodiment of the present invention;

FIG. 4 is a flowchart illustrating operations performed, such as by the image processing system of FIG. 3, in order to detect an anatomical marker within an image study in accordance with an example embodiment of the present invention; and FIG. 5 is a flowchart illustrating operations performed, such as by the image processing system of FIG. 3, in order to create a model of a plurality of image studies in accordance with an example embodiment of the present invention.

DETAILED DESCRIPTION

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

An image processing system, method and computer program product are provided for detecting a fiducial or an anatomical marker (hereinafter generally referenced as an "anatomical marker") within an image study. The image processing system, method and computer program product rely, not upon the picture elements (pixels) that comprise the image slices of an image study, but on other data elements that are representative of one or more characteristics of the image slices. For example, the image processing system, method and computer program product may rely upon data elements extracted from metadata associated with the individual image slices and/or the image study as a whole. Based upon an analysis of the characteristics of the image slices that are provided by the data elements, the desired anatomical marker may be detected within the image study in a more efficient manner in comparison to fiducial or anatomic landmark detection techniques that rely upon three-dimensional volumetric image processing of the picture elements of the image slices. As a result of the detection of the anatomical marker within the image study, the image processing system, method and computer program product facilitate the review of the image study by a physician or other health care professional in a manner that is efficient for the physician or other health care professional since they are able to more quickly identify and review the subset of image slices of the image study that are of most relevance. However, the reliance upon data elements representative of characteristics of the image slices without analysis of the picture elements of the image slices permits the image processing system, method and computer program product of an example embodiment to detect the anatomical marker in an efficient manner while consuming fewer processing resources and utilizing less memory.

Referring now to FIG. 1, a patient who is subjected to an image scan is depicted. As shown, the patient of this example is lying upon a table and an imaging system, such as a cross-sectional imaging modality, such as CT or MR imaging systems, captures a plurality of image slices of different portions of the patient with the image slices being combined to form an image study. The image study provides a three-dimensional volumetric image of the patient or at least the portion of the patient that was the subject of the image scan. In FIG. 1 in which the patient lies upon a table such that the height of the patient extends along a axis, the image slices are captured at a plurality of spaced apart locations along the a axis. Typically, the image slices are captured with a predefined step size between adjacent image slices. The step size is generally quite small such that the resulting image study includes hundreds or thousands of image slices. For purposes of illustration, however, an image study comprised of a fewer number of image slices (designated 1, 2, . . . 11) that are spaced apart by a larger step size is depicted in FIG. 1 with each vertical line 10 representative of a different image slice taken in the x-y plane that extends into and out of the page.

As shown in FIG. 2, an image study 20 is comprised of a plurality of image slices 22. Each image slice, in turn, includes the picture elements (pixels) 24 that comprise the actual image as well as a number of other data elements 26 that provide information associated with the particular image slice, such as data elements representative of one or more characteristics of the image slice. For example, each image slice may include metadata that includes the data elements and is associated with the picture elements. For example, as shown in FIG. 2, the image slices may include a header, such as a Digital Imaging and Communications in Medicine (DICOM) header, that includes the metadata that defines the data elements representative of various characteristics of the respective image slice. While shown as a header, the metadata may be stored in a footer or in some other form of data record associated with the picture elements of the respective image slice. Additionally or alternatively, the image study itself may include or otherwise be associated with metadata that defines various characteristics of the image study and/or individual image slices within the image study. Thus, the image study of this example embodiment may include a header 28, a footer or other data record that includes the data elements representative of one or more characteristics of the image study or individual image slices of the image study.

The data elements that are representative of one or more characteristics of the image slices may include any of a variety of different types of data elements. In an example embodiment, the data elements include parameters associated with the imaging system that captures the image slices including parameters that define the configuration of the imaging system during the capture of the respective image slices. For example, a CT imaging system includes electron tubes that generate the electrons necessary to create the image slices. In order to generate the electrons necessary to capture an image slice, the electron tube is driven with an electrical current (herein referenced as tube current). Many CT imaging systems include automatic tube current modulation (ATCM). ATCM is designed to maintain constant image quality regardless of the attenuation characteristics of the portion of the patient undergoing examination.

For example, the attenuation characteristics of a body part of a patient may depend upon the size of the patient and the particular body part. In this regard, adults who are larger generally introduce greater attenuation of the electron beam than does a smaller child. Additionally, bony structures, such as shoulders and the pelvis, more substantially attenuate the electron beam than other less bony structures, such as the lungs. Further, the presence of non-anatomical objects within a patient, such as a hip arthroplasty, artificial joints, pacemakers, wires, pins, dental fillings or other prosthetics may also increase the attenuation of the electron beam. ATCM therefore provides for the automatic adjustment of the tube current based upon the attenuation characteristics experienced by the electron beam during the capture of a respective image slice such that the resulting image quality remains constant regardless of the attenuation characteristics. Thus, during the capture of an image slice of the pelvis of a patient, the tube current may be increased in order to compensate for the increased attenuation characteristics of the pelvis, while the tube current may be reduced during the capture of an image slice through the lungs of the patient in order to compensate for the reduced attenuation characteristics of the lungs. As a result, each of the image slices has a similar image quality regardless of the attenuation characteristics.

With respect to FIG. 2, the curve 12 that extends through the vertical lines 10 representative of the plurality of image slices along the length of the patient illustrates the tube current in milliamperes (mA) that is provided to the electron tube during the capture of the various image slices. As shown, the tube current increases substantially during the capture of the image slices of the shoulder of the patient and the pelvis of the patient and is otherwise at a lower level so as to compensate for the different attenuation characteristics of the patient's body parts.

The tube current provided to the electron tube during the capture of a respective image slice is an example of a data element that is associated with the picture elements that comprise the image slice. In this regard, the tube current is representative of a characteristic of the image slice and, as such, may be stored in the header, such as a DICOM header, associated with the respective image slice. The data elements representative of characteristics of the respective image slice may include a variety of other data elements, such as data elements identifying the vendor name, such as the manufacturer identifier (ID), of the imaging system, the type of modality, such as CT, MR or the like, acquisition parameters, such as peak kilovoltage (kVP), slice thickness, gantry tilt value, exposure time, angular position, scan arc, size of field of view, frame of reference, slice number, image location and orientation, patient demographics including age and gender, as well as study/series information, such as protocol name, study/series description, examination/procedure description or the like. As these examples illustrate, the data elements may include parameters associated with the imaging system that captures the image slices including parameters that define the configuration of the imaging system during capture of the respective image slices. Following capture, the image study 20 including a plurality of image slices 22 may be stored, such as in a database or other memory.

In accordance with an example embodiment of the present invention, an image processing system is configured to detect an anatomical marker within an image study so as to facilitate the subsequent review of a subset of the image slices of the image study, such as by a physician or other health care professional. The image processing system may be embodied by any of a variety of different types of computing devices, such as servers, computer workstations, personal computers or other more specialized computer systems associated with the respective imaging modalities. Regardless of the manner in which the image processing system is embodied, the image processing system may be specifically configured in accordance with an example embodiment of the present invention.

In this regard, the image processing system 30 of FIG. 3 includes, is associated with or otherwise is in communication with processing circuitry 32 that is configurable to perform functions in accordance with one or more example embodiments disclosed herein. In this regard, the processing circuitry may be configured to perform and/or control performance of one or more functionalities of the image processing system or components thereof in accordance with various example embodiments, and thus may provide means for performing functionalities of the image processing system. The processing circuitry may be configured to perform data processing, application execution and/or other processing and management services according to one or more example embodiments.

In some example embodiments, the processing circuitry 32 includes a processor 34 and, in some embodiments, such as that illustrated in FIG. 3, further includes memory 36. The processing circuitry may also be in communication with or otherwise control a communication interface 38 for communicating with other computing systems and optionally a user interface 40 for interacting with a user, such as a healthcare professional. As such, the processing circuitry may be embodied as a circuit chip (e.g., an integrated circuit chip) configured (e.g., with hardware, software or a combination of hardware and software) to perform operations described herein.

The processor 34 may be embodied in a number of different ways. For example, the processor may be embodied as various processing means such as one or more of a central processing unit, a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor may comprise a plurality of processors. The plurality of processors may be in operative communication with each other and may be collectively configured to perform one or more functionalities of the computing device as described herein. The plurality of processors may be embodied on a single computing device or distributed across a plurality of computing devices collectively configured to function as the computing device. In some example embodiments, the processor may be configured to execute instructions stored in the memory 36 or otherwise accessible to the processor. As such, whether configured by hardware or by a combination of hardware and software, the processor may represent an entity (e.g., physically embodied in circuitry—in the form of processing circuitry 32) capable of performing operations according to embodiments of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform one or more operations described herein.

The processing circuitry 32 may also include memory 36 as shown in FIG. 3. In some example embodiments, the memory may include one or more non-transitory memory devices such as, for example, volatile and/or non-volatile memory that may be either fixed or removable. In this regard, the memory may comprise a non-transitory computer-readable storage medium. It will be appreciated that while the memory is illustrated as a single memory, the memory may comprise a plurality of memories. The memory may be configured to store information, data, applications, instructions and/or the like for enabling the computing device to carry out various functions in accordance with one or more example embodiments. For example, the memory may be configured to buffer input data, such as one or more image studies, for processing by the processor 34. Additionally or alternatively, the memory may be configured to store instructions for execution by the processor. Among the contents of the memory, applications may be stored for execution by the processor in order to carry out the functionality associated with each respective application. In some cases, the memory may be in communication with the processor via a bus or buses for passing information among components of the image processing system 30.

The image processing system 30 of the embodiment of FIG. 3 also includes a communication interface 38. For example, the communication interface may be configured to communicate with one or more imaging systems in order to receive the image studies. Additionally or alternatively, the communication interface may be configured to communication with one or more databases or other data repositories, a server or the like that stores the image studies and that provides them upon request to the image processing system. The communication interface may be any means such as a device or circuitry embodied in either hardware or a combination of hardware and software that is configured to receive and/or transmit messages from sources to subscribers. In this regard, the communication interface may include, for example, an antenna (or multiple antennas) and supporting hardware and/or software for enabling communications with a wireless communication network. Additionally or alternatively, the communication interface may include the circuitry for interacting with the antenna(s) to cause transmission of signals via the antenna(s) or to handle receipt of signals received via the antenna(s). In some environments, the communication interface may alternatively or also support wired communication.

In addition to the processing circuitry 32, the image processing system 30 may optionally include a user interface 40 for displaying and/or receiving data, content or the like. The user interface may include a display, a user input interface or the like. The user input interface, in turn, can include any of a number of devices allowing the computing device to receive data from a user, such as a microphone, a keypad, a touch-sensitive surface (integral or separate from the monitor), a joystick, or other input device. As will be appreciated, the processing circuitry may be directly connected to other components of the computing device, or may be connected via suitable hardware. In one example, the processing circuitry may be connected to the user interface via an adapter configured to permit the processing circuitry to send graphical information to the user interface.

Referring now to FIG. 4, the operations performed, such as by the image processing system 30 of FIG. 3, are depicted. As shown in block 50, the image processing system, such as the processing circuitry 32, e.g., the processor 34, the memory 36 or the like, is configured to access the data elements associated with image slices of the image study of a patient. These data elements may be stored, for example, in headers, such as DICOM headers, of each individual image slice and/or a header, such as a DICOM header, associated with the image study as a whole. As shown in block 52 of FIG. 4, the image processing system, such as the processing circuitry, e.g., the processor or the like, is also configured to review the data elements associated with at least some of the image slices and, in some instances, all of the image slices, of the image study of the patient. Based upon the review of the data elements, the image processing system, such as the processing circuitry, e.g., the processor or the like, is configured to detect the anatomical marker within the image study, as shown in block 54 of FIG. 4.

The review of the data elements and the resulting detection of the anatomical marker based upon the review of the data elements may be performed in various manners depending upon, for example, the anatomical marker of interest. For example, anatomical marker of interest may be a body part that has different attenuation characteristics than other neighboring body parts. For example, the anatomical marker may be the lungs of a patient in order to permit the subset of image slices that are representative of the lungs and the heart of the patient to be identified in comparison to other image slices representative of different body parts of the patient. As described above in conjunction with FIG. 1, the lungs generally introduce less attenuation than do the shoulders and pelvis of the patient. Since the tube current with which the electron tube is driven during the capture of the various image slices corresponds directly to the attenuation characteristics of the body part that is the subject of the image slice, the image processing system 30, such as the processing circuitry 32, of an example embodiment may review the tube current associated with the image slices of the image study and may detect the lungs, that is, the anatomical marker of this example, as lying within the region of the image study for which the image slices have a lower tube current than the tube current associated with the image slices on either side thereof, such as the image slices of the bony shoulders of the patient that have a higher tube current than the image slices of the lungs and the image slices of the pelvis of the patient that also have a higher tube current than the image slices of the lungs. Thus, in this example embodiment, the tube current associated with each image slice may be reviewed so as to detect the anatomical marker, that is, the lungs of the patient, as being within those image slices having a lower associated tube current than the image slices on either side thereof.

Based upon the identification of the anatomical marker or a distance from the anatomical marker, the image processing system 30, such as the processing circuitry 32, e.g., the processor 34 or the like, is configured to identify a subset of the image slices of the image study, such as a subset of the image slices of the image study that include the anatomical marker that was detected, as shown in block 56 of FIG. 4. In the foregoing example in which lungs of the patient were the anatomical marker to be detected, the image processing system may identify those image slices that are associated with the lower tube current and that lie between the image slices of the patient's bony shoulders and the patient's pelvis that have a higher tube current to be the subset of image slices that are of most potential relevance.

As shown in block 58 of FIG. 4, the image processing system 30 of an example embodiment, such as the processing circuitry 32, e.g., the processor 34, the user interface 40 or the like, may be configured to preferentially present the subset of the image slices that is identified, such as via the user interface, relative to other image slices of the image study. For example, a physician or other health care professional that accesses an image study and identifies the anatomical marker of interest may be presented, not with all of the image slices of the image study, but, instead, with the subset of image slices that include or is otherwise associated with (e.g., by being in a predefined location relative to) the designated anatomical marker. Consequently, the physician or other health care professional can focus their review upon the subset of image slices in order to more efficiently review the image study. The processing circuitry of other example embodiments may also preferentially perform other functions with respect to the identified subset of image slices, such as by preferentially storing the subset of image slices in memory 36.

In addition to or instead of identifying the subset of image slices based upon the anatomical marker in real time or near real time in response to input provided by a physician or other health care professional who is reviewing the image study, one or more subsets of image slices of the image study may be identified based upon one or more anatomical markers following the capture of the image study, but prior to the review of the image study by a physician or other health care professional. Thus, the subset(s) of the image slices of the image study may be stored, such as in memory 34, or flagged, such as by setting a flag in the header of the image study and/or the headers of its constituent image slices, so as to be readily accessed in response to a subsequent inquiry by a reviewing physician or other health care professional.

In addition to or instead of reviewing the data elements associated with characteristics of a single respective image slice, the image processing system 30 of an example embodiment may be configured to review the data elements by determining a rate of change of one or more parameters associated with the imaging system from one image slice to another, such as the rate of change of a respective parameter between adjacent image slices, such as between Image Slice i and Image Slice i+1. With respect to the foregoing example in which the tube current is reviewed, the image processing system, such as the processing circuitry 32, of this example embodiment is configured to determine the rate of change of the tube current from one image slice to the next image slice. The rate of change may be in the form, for example, of a first derivative of a respective type of data element, a second derivative of the respective type of data element or the like. The image processing system, such as the processing circuitry, of this example embodiment may therefore be configured to detect the anatomical marker based at least in part upon the rate of change of respective type of data element. In the foregoing example in which the tube current is reviewed, the image processing system, such as the processing circuitry, is configured to review the rate of change of the tube current and to identify the portion of the image study that is representative of the lungs based, at least in part, upon the rate of change of the tube current. In this regard, the transition from the image slices of the shoulders of the patient to the image slices representative of the lungs of the patient may be identified by relatively large negative rate of change of the tube current as shown, for example, by segment 12a of curve 12 of FIG. 1. Similarly, the transition from the image slices of the lungs of the patient to the image slices of the pelvis of the patient may be identified by a relatively large positive rate of change of the tube current as shown, for example, by segment 12b of curve 12 of FIG. 1.

While the foregoing example relies upon tube current as the data element to be reviewed in conjunction with the identification of the anatomical marker, the image processing system 30 and method may review different types of data elements and combinations of different types of data elements in order to identify anatomical markers in other example embodiments.

In regards to the review of the data elements, the image processing system 30 and method may be configured to review the data elements by comparing the data elements to predefined threshold values and/or to the values of data elements of other image slices of the image study. In an example embodiment, however, a model of a particular type of image study, such as a CT scan of an adult abdomen, may be created and may be used as the point of comparison during the review of the data elements. In this example embodiment, the image processing system, such as the processing circuitry 32, e.g., the processor 34 or the like, is configured to collect or otherwise access the data elements associated with the image slices of a plurality of image studies of the same type, such as image studies of the torso of various different patients captured by the same type or different types of imaging systems. See block 60 of FIG. 5. In this example embodiment, the image processing system, such as the processing circuitry, e.g., the processor or the like, is also configured to separately normalize each different type of data element, such as tube current, kVP or other acquisition parameters, such as between different types of patients, e.g., between adults and children, and/or between the image studies captured by different imaging systems, e.g., CT imaging systems vs. MR imaging systems. See block 62 of FIG. 5. As such, variations in the different types of data elements that are dependent upon factors other than the anatomy of the patient may be eliminated or at least reduced by the normalization of the different types of data elements.

In this example embodiment, the image processing system 30, such as the processing circuitry 32, e.g., the processor 34 or the like, is also configured to combine the data elements, following normalization, such as by separately combining the different types of data elements along the length of the patient or along the length of the body part of the patient that is the subject of the image study to create a model of the image studies. See block 64 of FIG. 5. For example, the normalized tube current of the image slices of the plurality of image studies of adult torsos may be averaged along the length of the patient or along the length of the body part of the patient that is the subject of the image study. Similarly, the other types of data elements of the image slices may be combined, e.g., averaged, along the length of the patient or along the length of the body part of the patient that is the subject of the image study. Thus, the model that is created may define profiles of the various data elements along the length of the patient or along the length of the body part of the patient that is the subject of the image study with the profile of the data elements being based, for example, upon averages of the respective data elements from a plurality of different image studies at each of a plurality of different locations along the length of the patient.

Once the model has been created, the image processing system 30, such as the processing circuitry 32, e.g., the processor 34 or the like, may be configured to review the data elements in an effort to identify the anatomical marker of interest by comparing the data element(s) of an image study of interest to the model that has been created. Within the model, different anatomical markers may have been identified relative to the various data elements, such as described above with respect to the tube current depicted in FIG. 1. Thus, by reviewing the data elements and identifying those image slices within the image study of interest that have data elements that correspond, such as by being similar or varying in a similar manner to, the data elements of the model that are associated with the anatomical marker of interest, the anatomical marker may be identified based upon the comparison of the data elements of the image study of interest to the model.

In an example embodiment, the model may be constructed from a plurality of similar image studies, such as image studies of the same type. Thereafter, the model may be trained, such as by a neural network or other classifier, e.g., a random force classifier or the like, based upon one or more additional image studies, that is, a training set of image studies. Once trained, the model may be tested utilizing an evaluation set of image studies. As such, the resulting model may then be utilized to review the data elements of an image study of interest in order to accurately identify an anatomical marker within the image study of interest.

A method, image processing system 30 and computer program product are therefore provided in order to detect an anatomical marker within an image study. As described, the method, image processing system and computer program product may be configured to detect an anatomical marker based upon data elements that are representative of one or more characteristics of the image slices, but that do not include picture elements. Thus, the method, image processing system and computer program product may detect an anatomical marker in a more timely and efficient manner. Consequently, the processing resources required to detect an anatomical marker may be conserved, while still permitting a subset of the image slices of the image study to be reliably identified based upon the anatomical marker, such as for storage, display or the like. The identified subset of image slices may be utilized for various purposes to improve user efficiency including, for example, z-direction registration, anatomy-based starting points for linked scrolling, optimization for window-leveling presentation, verification of study examination descriptions, definition of rules for re-grouping image slices, qualifying technologist acquisition, serving as a protocol against a benchmark as part of quality assurance checks, etc.

As described above, FIGS. 4 and 5 illustrate flowcharts of an image processing system 30, method and computer program product according to example embodiments of the invention. It will be understood that each block of the flowcharts, and combinations of blocks in the flowcharts, may be implemented by various means, such as hardware, firmware, processor, circuitry, and/or other communication devices associated with execution of software including one or more computer program instructions. For example, one or more of the procedures described above may be embodied by computer program instructions. In this regard, the computer program instructions which embody the procedures described above may be stored by a memory device 36 of an image processing system employing an embodiment of the present invention and executed by a processor 34 of the image processing system. As will be appreciated, any such computer program instructions may be loaded onto a computer or other programmable apparatus (for example, hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks.

Accordingly, blocks of the flowchart support combinations of means for performing the specified functions and combinations of operations for performing the specified functions for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In some embodiments, certain ones of the operations above may be modified or further amplified. Furthermore, in some embodiments, additional optional operations may be included, some of which have been described above. Modifications, additions, or amplifications to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method for detecting an anatomical marker within an image study, the method comprising:
   normalizing data elements associated with image slices of a plurality of image studies;
   combining the data elements, following normalization, to create a model of the image studies;
   accessing data elements associated with image slices of the image study of a patient, wherein the data elements are representative of one or more characteristics of the image slices but do not include picture elements that comprise the image slices;
   reviewing the data elements associated with at least some image slices of the image study of the patient by comparing the data elements to the model;
   detecting the anatomical marker within the image study based upon a review of the data elements; and
   identifying a subset of the image slices of the image study based upon the anatomical marker or a distance from the anatomical marker.

2. A method according to claim 1 further comprises causing the subset of the image slices to be preferentially presented relative to other image slices of the image study.

3. A method according to claim 1 wherein accessing data elements comprise accessing metadata associated with the image slices of the image study, wherein the metadata includes the data elements.

4. A method according to claim 1 further comprising capturing the image slices with the imaging system in accordance with the configuration defined by the one or more parameters.

5. A method according to claim 1 wherein the data elements also include one or more parameters associated with an imaging system that captures the image slices including one or more parameters that define a configuration of the imaging system during capture of the respective image slices.

6. A method according to claim 5 wherein the data element associated with a respective image slice comprises a tube current at which the respective image slice was captured.

7. A method according to claim 5 wherein reviewing the data elements comprises determining a rate of change of one or more parameters associated with two or more image slices, and wherein detecting the anatomical marker comprises detecting the anatomical marker based at least in part upon the rate of change.

8. An image processing system configured to detect an anatomical marker within an image study, the image processing system comprising processing circuitry configured to:
   normalize data elements associated with image slices of a plurality of image studies;
   combine the data elements, following normalization, to create a model of the image studies;
   access data elements associated with image slices of the image study of a patient, wherein the data elements are representative of one or more characteristics of the image slices but do not include picture elements that comprise the image slices;
   review the data elements associated with at least some image slices of the image study of the patient by comparing the data elements to the model;
   detect the anatomical marker within the image study based upon a review of the data elements; and
   identify a subset of the image slices of the image study based upon the anatomical marker or a distance from the anatomical marker.

9. An image processing system according to claim 8 wherein the processing circuitry is further configured to cause the subset of the image slices to be preferentially presented relative to other image slices of the image study.

10. An image processing system according to claim 8 wherein the processing circuitry is configured to access data elements by accessing metadata associated with the image slices of the image study, wherein the metadata includes the data elements.

11. An image processing system according to claim 8 wherein the data elements also include one or more parameters associated with an imaging system that captures the image slices including one or more parameters that define a configuration of the imaging system during capture of the respective image slices.

12. An image processing system according to claim 11 wherein the data element associated with a respective image slice comprises a tube current at which the respective image slice was captured.

13. An image processing system according to claim 11 wherein the processing circuitry is configured to review the data elements by determining a rate of change of one or more parameters associated with two or more image slices, and wherein the processing circuitry is configured to detect the anatomical marker by detecting the anatomical marker based at least in part upon the rate of change.

14. A computer program product for detecting an anatomical marker within an image study, the computer program product comprising at least one non-transitory computer-readable storage medium bearing computer program instructions embodied therein for use with a computer, the computer program instructions comprising program instructions which, when executed, cause the computer at least to:
   normalize data elements associated with image slices of a plurality of image studies;
   combine the data elements, following normalization, to create a model of the image studies;
   access data elements associated with image slices of the image study of a patient, wherein the data elements are representative of one or more characteristics of the image slices but do not include picture elements that comprise the image slices;
   review the data elements associated with at least some image slices of the image study of the patient by comparing the data elements to the model;
   detect the anatomical marker within the image study based upon a review of the data elements; and
   identify a subset of the image slices of the image study based upon the anatomical marker or a distance from the anatomical marker.

15. A computer program product according to claim 14 wherein the computer program instructions further comprise program instructions configured to cause the subset of the image slices to be preferentially presented relative to other image slices of the image study.

16. A computer program product according to claim 14 wherein the program instructions configured to access data elements comprise program instructions configured to access metadata associated with the image slices of the image study, wherein the metadata includes the data elements.

17. A computer program product according to claim 14 wherein the data element associated with a respective image slice comprises a tube current at which the respective image slice was captured.

18. A computer program product according to claim 14 wherein the program instructions configured to review the data elements comprise program instructions configured to determine a rate of change of one or more parameters associated with two or more images slices, and wherein the program instructions configured to detect the anatomical marker comprise program instructions configured to detect the anatomical marker based at least in part upon the rate of change.

19. A computer program product according to claim 14 wherein the data elements also include one or more parameters associated with an imaging system that captures the image slices including one or more parameters that define a configuration of the imaging system during capture of the respective image slices.

* * * * *

UNITED STATES PATENT AND TRADEMARK OFFICE
CERTIFICATE OF CORRECTION

PATENT NO. : 10,078,726 B2
APPLICATION NO. : 15/086725
DATED : September 18, 2018
INVENTOR(S) : Noordvyk et al.

Page 1 of 1

It is certified that error appears in the above-identified patent and that said Letters Patent is hereby corrected as shown below:

In the Claims

Column 16,
Line 46, "two or more images slices" should read --two or more image slices--.

Signed and Sealed this
Second Day of April, 2019

Andrei Iancu
*Director of the United States Patent and Trademark Office*